(12) United States Patent
Sato et al.

(10) Patent No.: US 10,092,334 B2
(45) Date of Patent: Oct. 9, 2018

(54) FEMUR FIXATION APPARATUS

(71) Applicant: OMIC CORPORATION, Ritto-shi, Shiga (JP)

(72) Inventors: Toru Sato, Ritto (JP); Kouji Imoto, Ritto (JP); Minoru Ito, Ritto (JP)

(73) Assignee: OMIC CORPORATION, Ritto-shi (JP)

( * ) Notice: Subject to any disclaimer, the term of this patent is extended or adjusted under 35 U.S.C. 154(b) by 0 days.

(21) Appl. No.: 15/560,669

(22) PCT Filed: Dec. 27, 2016

(86) PCT No.: PCT/JP2016/088828
§ 371 (c)(1),
(2) Date: Sep. 22, 2017

(87) PCT Pub. No.: WO2018/042688
PCT Pub. Date: Mar. 8, 2018

(65) Prior Publication Data
US 2018/0250042 A1 Sep. 6, 2018

(30) Foreign Application Priority Data
Sep. 1, 2016 (WO) .................. PCT/JP2016/075675

(51) Int. Cl.
*A61B 17/74* (2006.01)
*A61B 17/72* (2006.01)
*A61B 17/86* (2006.01)

(52) U.S. Cl.
CPC ........ *A61B 17/744* (2013.01); *A61B 17/7233* (2013.01); *A61B 17/86* (2013.01)

(58) Field of Classification Search
CPC .... A61B 17/72–17/7291; A61B 17/74–17/748
See application file for complete search history.

(56) References Cited

U.S. PATENT DOCUMENTS 8,100,911 B2 * 1/2012 Yamazaki .......... A61B 17/7241
606/301
8,491,584 B1 * 7/2013 Fagan .................. A61B 17/744
606/64

(Continued)

FOREIGN PATENT DOCUMENTS

JP 2002-035000 A 2/2002
JP 2010-530791 A 9/2010

(Continued)

OTHER PUBLICATIONS

Mar. 21, 2017 Search Report issued in International Patent Application No. PCT/JP2016/088828.

(Continued)

*Primary Examiner* — Eduardo C Robert
*Assistant Examiner* — Michelle C Eckman
(74) *Attorney, Agent, or Firm* — Oliff PLC

(57) ABSTRACT

A femur fixation apparatus includes an intramedullary nail, a lag screw that is inserted through the intramedullary nail, and an adjuster 4 fitted in the intramedullary nail. The adjuster includes a sliding part unrotatable and slid-movable in a longitudinal direction relative to the intramedullary nail and a rotation part rotatably connected to the sliding part. A lower end of the rotation part is formed with an inward flange part and a cutout. An engaging part of an engaging protrusion formed to the sliding part is inserted into the rotation part via the cutout from the radial direction, and the engaging part is supported by the inward flange part from the bottom, rotatably connecting the sliding part to the rotation part.

3 Claims, 17 Drawing Sheets

(56) References Cited

U.S. PATENT DOCUMENTS

| | | | |
|---|---|---|---|
| 8,790,343 B2* | 7/2014 | McClellan | A61B 17/7241 606/64 |
| 9,084,643 B2* | 7/2015 | Mikhail | A61B 17/72 |
| 9,295,504 B2* | 3/2016 | Haidukewych | A61B 17/7241 |
| 9,757,169 B2* | 9/2017 | Boraiah | A61B 17/744 |
| 9,782,206 B2* | 10/2017 | Mueckter | A61B 17/744 |
| 2002/0032445 A1* | 3/2002 | Fujiwara | A61B 17/744 606/67 |
| 2002/0156473 A1* | 10/2002 | Bramlet | A61B 17/725 606/62 |
| 2005/0069397 A1 | 3/2005 | Shavit et al. | |
| 2005/0143739 A1* | 6/2005 | Shinjo | A61B 17/744 606/62 |
| 2005/0203510 A1* | 9/2005 | Sohngen | A61B 17/744 606/60 |
| 2006/0200160 A1* | 9/2006 | Border | A61B 17/72 606/88 |
| 2006/0241604 A1* | 10/2006 | Frigg | A61B 17/744 606/62 |
| 2008/0140077 A1* | 6/2008 | Kebaish | A61B 17/744 606/64 |
| 2008/0183171 A1* | 7/2008 | Elghazaly | A61B 17/7241 606/64 |
| 2008/0262498 A1* | 10/2008 | Fernandez Dell'Oca | A61B 17/744 606/65 |
| 2009/0048600 A1* | 2/2009 | Matityahu | A61B 17/7241 606/62 |
| 2009/0248025 A1* | 10/2009 | Haidukewych | A61B 17/744 606/67 |
| 2010/0121327 A1* | 5/2010 | Velikov | A61B 17/744 606/65 |
| 2010/0174284 A1* | 7/2010 | Schwammberger | A61B 17/7283 606/62 |
| 2010/0249781 A1 | 9/2010 | Haidukewych et al. | |
| 2011/0196370 A1 | 8/2011 | Mikhail | |
| 2011/0196372 A1* | 8/2011 | Murase | A61B 17/744 606/64 |
| 2012/0143192 A1* | 6/2012 | Watanabe | A61B 17/7225 606/64 |
| 2012/0191092 A1* | 7/2012 | Buettler | A61B 17/744 606/64 |
| 2012/0197255 A1* | 8/2012 | Elghazaly | A61B 17/725 606/64 |
| 2013/0261622 A1* | 10/2013 | Bonjour | A61B 17/7233 606/64 |
| 2014/0012259 A1* | 1/2014 | Matityahu | A61B 17/748 606/62 |
| 2014/0052132 A1* | 2/2014 | Matityahu | A61B 17/1725 606/62 |
| 2014/0214098 A1* | 7/2014 | Probe | A61B 17/744 606/306 |
| 2014/0330274 A1* | 11/2014 | Matityahu | A61B 17/748 606/64 |
| 2015/0038967 A1* | 2/2015 | Khong | A61B 17/164 606/64 |
| 2015/0038968 A1* | 2/2015 | Vega | A61B 17/7266 606/64 |
| 2015/0157369 A1* | 6/2015 | Ehmke | A61B 17/7241 606/64 |
| 2017/0202584 A1* | 7/2017 | Hientzsch | A61B 17/3472 |
| 2018/0078299 A1* | 3/2018 | Rossney | A61B 17/72 |

FOREIGN PATENT DOCUMENTS

| | | |
|---|---|---|
| JP | 2012-507355 A | 3/2012 |
| JP | 2013-009803 A | 1/2013 |
| JP | 2015-73843 A | 4/2015 |
| JP | 5961774 B1 | 8/2016 |

OTHER PUBLICATIONS

Mar. 21, 2017 Written Opinion issued in International Patent Application No. PCT/JP2016/088828.

* cited by examiner

FIG. 13
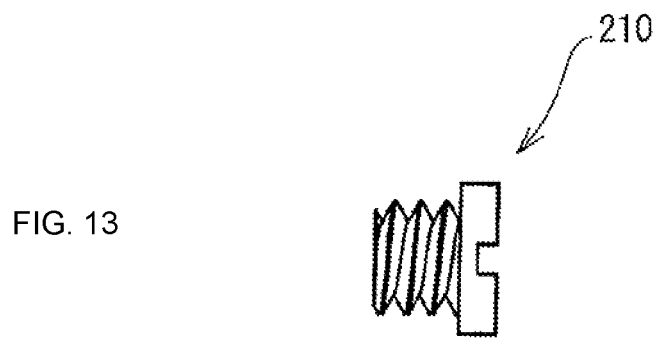
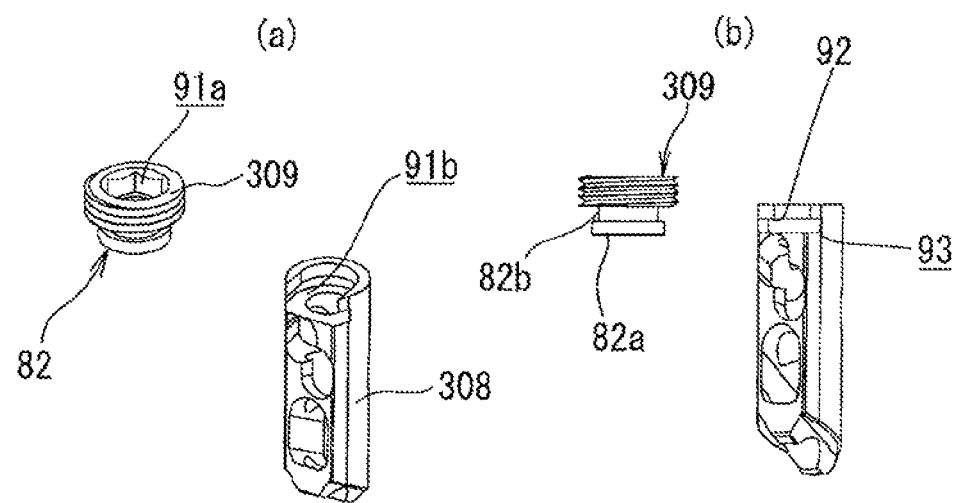
FIG. 14

FEMUR FIXATION APPARATUS

TECHNICAL FIELD

The present invention relates to femur fixation apparatuses for use when fractures occur in proximal femur.

BACKGROUND

Along with the recent growth of the aging population, the number of cases of proximal femur fractures is increasing in the elderly, and bone fixation treatments with bone fixation apparatuses are widely performed. Since reduction at an early stage in bone fixation treatment and fixation methods have a huge effect on postoperative process, bone fixation apparatuses used for femoral neck fractures or femoral trochanter fractures with a firm fixing force are needed to maintain reduced position. A femur fixation apparatus disclosed in Patent Document 1 is an example of such bone fixation apparatuses.

FIGS. 17 and 18 show a femur fixation apparatus of Patent Document 1. This femur fixation apparatus 1A includes a lag screw (a femoral neck threaded rod part) 2A that is inserted into a bone including a femoral head of a fractured femur and an intramedullary nail (intramedullary rod part) 3A that is inserted with the lag screw 2A and inserted into a femoral shaft. An adjuster 4A is installed in the intramedullary nail 3A, and a stopper 40A formed to the lower end of the adjuster 4A engages with one of grooves 22A formed in the lag screw 2A, thereby preventing rotation of the lag screw 2A in its circumferential direction.

The adjuster 4A has a cylindrical part 8A threadedly engaged with an inner surface of the intramedullary nail 3A, a screw rotation part 9A supported to be rotatable in the circumferential direction but immovable up and down with respect to the cylindrical part 8A, and a sliding part (rotation prevention part) 10A threadedly engaged with the screw rotation part 9A. The sliding part 10A is unrotatable with respect to the intramedullary nail 3A. When a surgeon rotates the screw rotation part 9A with such operation tool as wrench, the sliding part 10A slides in an up-down direction relative to the intramedullary nail 3A. The stopper 40A is formed to the lower end of the sliding part 10A. Slide-moving the sliding part 10A downward engages the stopper 40A with the groove 22A of the lag screw 2A.

Also, an end cap 5A is mounted at the upper end of the intramedullary nail 3A. The end cap 5A has a male screw part 51A for threadedly engaging with a female screw part 81A of the cylindrical part 8A.

The femur fixation apparatus 1A further includes three rotation-prevention pins (femoral neck threaded rod auxiliary part) 61A and is configured to prevent a fractured segment from being dislocated in three-dimensional directions with the rotation-prevention pins 61A inserted into the femur and through the intramedullary nail 3A. Also, the sliding part 10A of the adjuster 4A is formed with an interference prevention hole and/or an interference prevention groove for preventing interference with the rotation-prevention pins 61A.

On the other hand, osteosynthesis devices disclosed in Patent Document 2 include a set screw fitted in an intramedullary nail and an end cap, and is configured to fix a lag screw in place with a protrusion formed to the end of the set screw and to fix a sub pin in place with a protrusion of the end cap inserted through the set screw. The set screw has a head part (a rotation part) with a fitting piece and a body part (a sliding part) formed with a fitting groove. The head part is pressed into the body part from a longitudinal direction of the body part with a specialized tool so that the fitting part of the head part is fitted into the fitting groove of the body part. As a result, the body part is attached to the head part so as to be freely rotatable but inseparable against certain force. Also, the head part of the set screw is formed with a slit penetrating from an inner peripheral surface to an outer peripheral surface. After the head part is fitted to the body part, the slit is slightly widened to enhance the resistance between the head part and a screw groove of the intramedullary nail.

Also, one way sliding devices for intertrochanteric fixation implants disclosed in Patent Document 3 are devices for treating fractures, including an intramedullary member sized and shaped for insertion along a longitudinal axis of a bone within a medullary canal thereof.

RELATED ART

Patent Documents

Patent Document 1: Japanese Patent Application Publication No. 2015-73843
Patent Document 2: Japanese Patent No. 5961774
Patent Document 3: Japanese Patent Application Publication No. 2012-507355

SUMMARY

Problems to be Solved by Invention

In the structure of the femur fixation apparatus of Patent Document 1, it is difficult to greatly increase the length of the sliding part. Also, the osteosynthesis device of Patent Document 2 requires the specialized tool to fit the head part to the body part of the set screw, complicating manufacturing processes. Also, there is a danger that the body part is detached from the head part. Further, in the one way sliding device of Patent Document 3 with a second element having a space in a central portion thereof for accommodating a ball of a first element, an opening should be smaller than a diameter of the ball so that the ball may be snapped into the space via the opening and the ball may not become easily disengaged therefrom.

It is an object of the invention to provide a femur fixation apparatus that widens the choice of rotation prevention members to use according to type of femur fracture.

It is another object of the invention to provide a femur fixation apparatus excellent in operability and reliability and easy to manufacture.

Means to Solve the Problems

According to one aspect of the invention, a femur fixation apparatus includes an intramedullary nail formed with at least one auxiliary hole for insertion of a rotation prevention member, a lag screw that is inserted through the intramedullary nail, and an adjuster fitted in the intramedullary nail, wherein: the adjuster includes a sliding part unrotatable and slide-movable in a longitudinal direction relative to the intramedullary nail and a rotation part rotatably connected to an upper part of the sliding part, the sliding part being formed with an interference prevention part for preventing interference with the rotation prevention member inserted through the auxiliary hole, the sliding part being formed at a lower end with a stopper that prevents rotation of the lag screw, the rotation part rotatably and threadedly engaged inside the intramedullary nail;

one of the sliding part and the rotation part is formed with an engaging protrusion; the other of the sliding part and the rotation part is formed with a receiving hole; the engaging protrusion includes an engaging part and a connecting part with a smaller diameter than the engaging part, the connecting part connecting the engaging part with the one of the sliding part and the rotation part; an opening edge of the receiving hole is formed with an inward flange part, and a peripheral surface of the receiving hole is formed with a cutout for receiving the engaging part from a radial direction of the adjuster, the cutout having a width dimension larger than an outer diameter of the engaging part; and when the engaging part is inserted in the receiving hole via the cutout from the radial direction of the adjuster, the sliding part is rotatably connected to the rotation part with the engaging part and the inward flange part confronting each other in the longitudinal direction.

According to another aspect of the invention, a femur fixation apparatus includes an intramedullary nail formed with at least one auxiliary hole for insertion of a rotation prevention member, a lag screw that is inserted through the intramedullary nail, and an adjuster fitted in the intramedullary nail, wherein: the adjuster includes a sliding part unrotatable and slide-movable in a longitudinal direction relative to the intramedullary nail and a rotation part rotatably connected to an upper part of the sliding part, the sliding part being formed with an interference prevention part for preventing interference with the rotation prevention member inserted through the auxiliary hole, the sliding part being formed at a lower end with a stopper that prevents rotation of the lag screw, the rotation part rotatably and threadedly engaged inside the intramedullary nail; one of the sliding part and the rotation part is formed with an engaging protrusion; the other of the sliding part and the rotation part is formed with a receiving hole; the engaging protrusion includes an engaging part and a connecting part with a smaller diameter than the engaging part, the connecting part connecting the engaging part with the one of the sliding part and the rotation part; an opening edge of the receiving hole is formed with an inward flange part, and the radial center of the engaging part is deviated from the radial center of an opening of the receiving hole; and the engaging part is inserted into the receiving hole in the longitudinal direction and then shifted in the radial direction of the adjuster to confront the inward flange part in the longitudinal direction, thereby rotatably connecting the slide part with the rotation part.

According to a different aspect of the invention, a femur fixation apparatus includes an intramedullary nail formed with at least one auxiliary hole for insertion of a rotation prevention member, a lag screw that is inserted through the intramedullary nail, and an adjuster fitted in the intramedullary nail, wherein: the adjuster includes a sliding part unrotatable and slide-movable in a longitudinal direction relative to the intramedullary nail and a rotation part rotatably connected to an upper part of the sliding part, the sliding part being formed with an interference prevention part for preventing interference with the rotation prevention member inserted through the auxiliary hole, the sliding part being formed at a lower end with a stopper that prevents rotation of the lag screw, the rotation part rotatably and threadedly engaged inside the intramedullary nail; one of the sliding part and the rotation part is formed with an engaging protrusion; the other of the sliding part and the rotation part is formed with a receiving hole; the engaging protrusion includes an engaging part and a connecting part with a smaller diameter than the engaging part, the connecting part connecting the engaging part with the one of the sliding part and the rotation part; a plurality of set screws is radially-inwardly inserted through an opening edge of the receiving hole; and the sliding part is rotatably supported by the rotation part with the engaging part received in the receiving hole confronting tip ends of the plurality of set screws in the longitudinal direction.

Effects of the Invention

According to the femur fixation apparatus of one aspect of the invention, because the engaging part is inserted into the receiving hole via the cutout from the radial direction that differs from the longitudinal direction of the sliding part by 90 degrees and confronts the inward flange part in the longitudinal direction, there is no danger that the sliding part is disengaged from the rotation part, and thus rotatable state is stably maintained. This makes it possible to provide a femur fixation apparatus with improved operability and reliability.

Also, the rotation part of the adjuster is threadedly and rotatably engaged inside the intramedullary nail, and the sliding part is rotatably connected to the rotation part. Thus, it is possible to increase the length of the sliding part without increasing the length of the entire adjuster. Because the interference prevention part for preventing interference with the rotation prevention member is formed to the sliding part, increasing the length of the sliding member widens the choice of the number of the rotation prevention members to use and the choice of insertion angles thereof, enabling an operation more suitable for type of femur fracture. Also, using a plurality of rotation preventing members with different angles fixes fractured femur more firmly and realizes excellent osteosynthesis.

Also, because the sliding part can be brought into connection with the rotation part without being pressed with a specialized tool nor the cutout being deformed, the adjuster can be manufactured easily. Also, because the configuration of the entire adjuster can be simpler, the number of parts thereof is decreased, reducing the manufacturing cost and improving stability of quality.

According to the femur fixation apparatus in the another aspect of the invention, because the radial center of the engaging part is deviated from the radial center of the opening of the receiving hole, inserting the engaging part into the receiving hole and then shifting the same in the radial direction of the adjuster rotatably connects the sliding part to the rotation part. Thus, there is no danger that the sliding part is disengaged from the rotation part. Also, there is no need to use a specialized tool for connecting the rotation part and the sliding part with each other.

According to the femur fixation apparatus in the different aspect of the invention, because the engaging part confronts the tip ends of the plurality of set screws in the longitudinal direction, there is no need to use the specialized tool in this configuration also, and there is no danger that the rotation part is disengaged from the sliding part.

BRIEF DESCRIPTION OF THE DRAWINGS

FIG. 13 A view showing a set screw used in the adjuster of FIG. 11

FIG. 14 Views of an adjuster according to a modification of the first embodiment of the invention, wherein (a) is an exploded perspective view, and (b) is an exploded front view FIG. 15 Views of an adjuster according to a modification of the second embodiment of the invention, wherein (a) is a front view of a rotation part of the adjuster, and (b) is an exploded perspective view of the adjuster FIG. 16 Views of an adjuster according to a modification of the third embodiment of the invention, wherein (a) is an exploded perspective view, and (b) is an exploded front view, and (c) is a front view FIG. 17 A perspective view of a conventional femur fixation apparatus FIG. 18 A cross-sectional view of significant parts of the femur fixation apparatus of FIG. 17

DETAILED DESCRIPTION

First Embodiment

Figure 1:
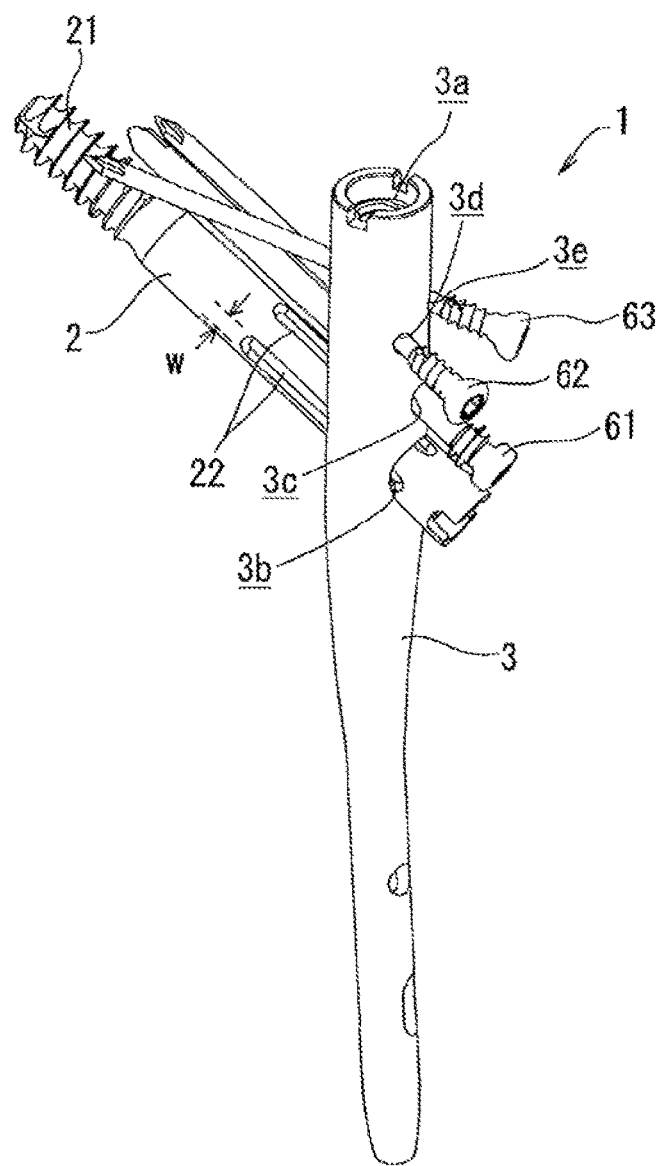
FIG. 1 A perspective view of a femur fixation apparatus according to a first embodiment of the invention FIG. 2 A partial cross-sectional view of the femur fixation apparatus of FIG. 1
Figure 2:
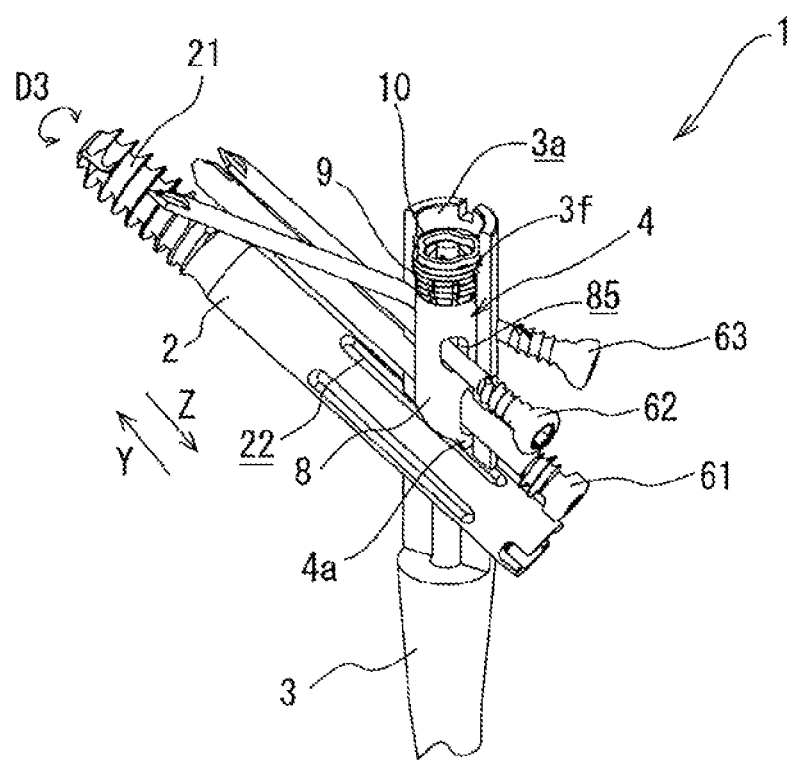
Figure 3:
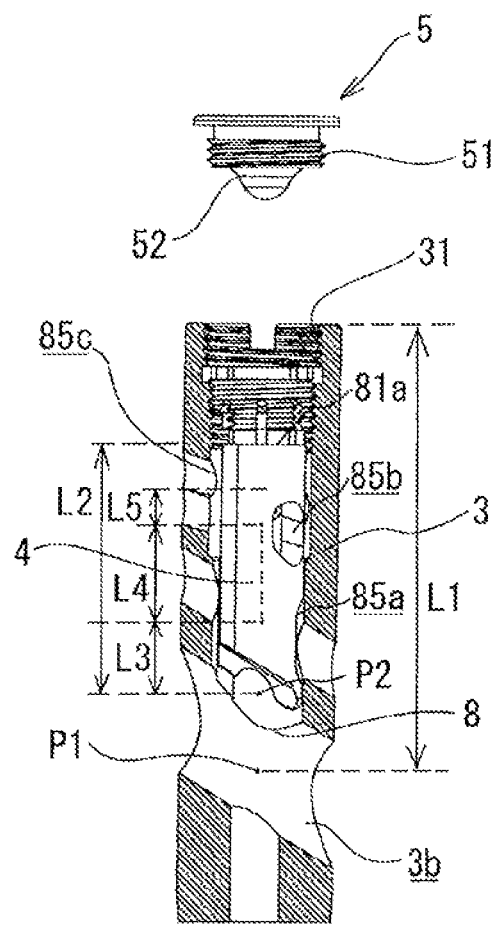
FIG. 3 A cross-sectional view of significant parts of the femur fixation apparatus of FIG. 1

A femur fixation apparatus according to a first embodiment of the invention will be described while referring to the accompanying drawings. With reference to FIGS. 1 to 3, a femur fixation apparatus 1 according to the embodiment is for use when proximal femoral fractures occur, and includes a lag screw 2 that is inserted into a bone including a head of a fractured femur, an intramedullary nail 3 that is inserted into a femoral shaft, an adjuster 4 fitted in the intramedullary nail 3, an end cap (cover member) 5 that is threadedly fitted to the upper end of the intramedullary nail 3, and one or more rotation prevention pins (in this example, three rotation prevention pins (rotation prevention members) 61, 62, 63) that is inserted through the intramedullary nail 3.

Note that in the following explanation, the great trochanter side is described as the upper side, and the distal end side is described as the lower side, assuming that the femur fixation apparatus 1 is placed in the femur in a predetermined manner.

The lag screw 2 is formed at one end with a male screw part 21, and the lag screw 2 is formed at the other end with a plurality of grooves 22 extending along a longitudinal direction of the lag screw 2 at intervals in a circumferential direction D3. The width dimension W of each groove 22 gradually increases toward the one end formed with the male screw part 21 and gradually decreases toward the inner side of the lag screw 2 in the radial direction (depth direction).

Figure 7:
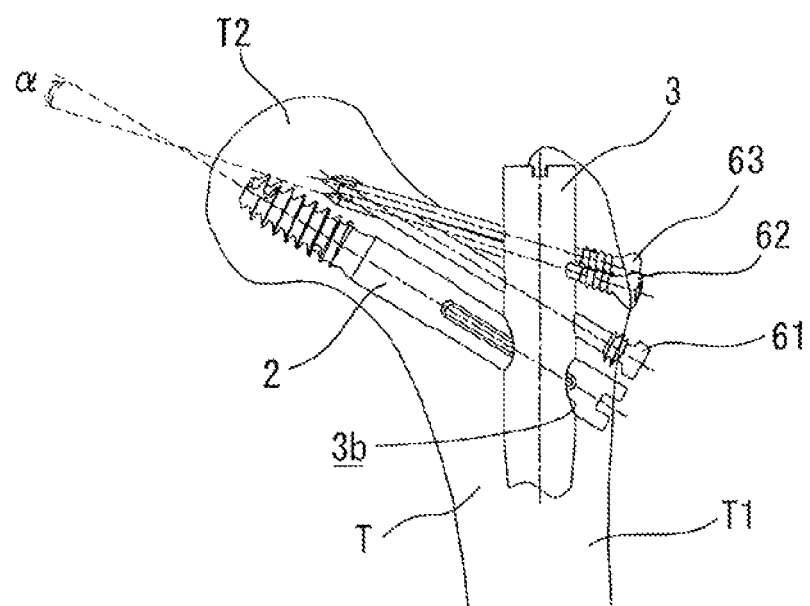
FIG. 7 A view showing the femur fixation apparatus of FIG. 1 used for a femur

The intramedullary nail 3 is formed with a long hole 3a, a through hole 3b, and at least one auxiliary hole (in this embodiment, three auxiliary holes 3c, 3d, 3e). The long hole 3a extends along the longitudinal direction of the intramedullary nail 3, and is formed at an upper end of an inner surface with a female screw part 31 that threadedly engages a male screw part 51 of the end cap 5 as shown in FIG. 3. The through hole 3b and the auxiliary holes 3c to 3e are for receiving the lag screw 2 and the rotation prevention pins 61 to 63, respectively, and are formed so as to penetrate a peripheral surface of the intramedullary nail 3. The length of the rotation prevention pins 61 to 63 is set such that their tip ends reach a femoral head T2 when inserted into the femur T in a predetermined manner as shown in FIG. 7.

The adjuster 4 is fitted inside the long hole 3a of the intramedullary nail 3. The adjuster 4 is formed at the lower end with a stopper 4a. Engaging the stopper 4a with any one of the grooves 22 of the lag screw 2 prevents rotation of the lag screw 2 in the circumferential direction D3.

Figure 4:
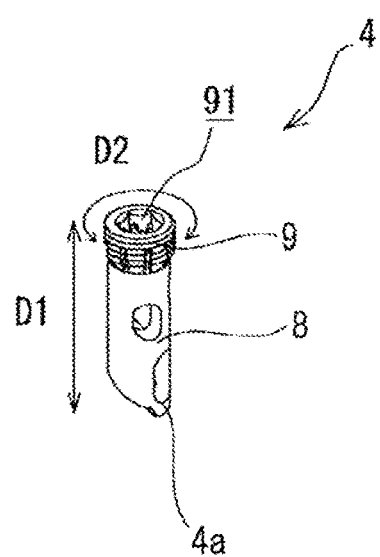
FIG. 4 A perspective view of an adjuster of the femur fixation apparatus of FIG. 1
Figure 5:
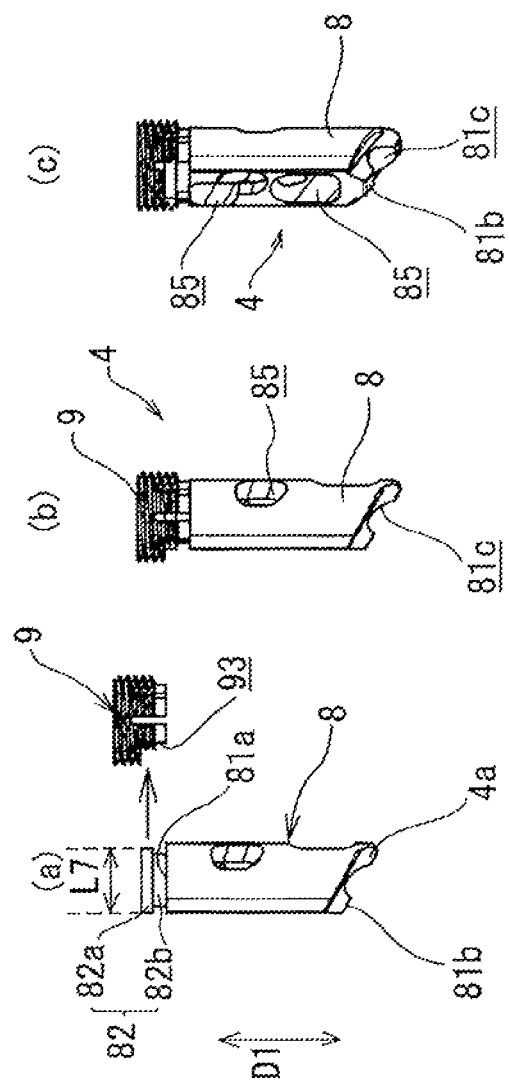
FIG. 5 Views of the adjuster of FIG. 1, wherein (a) is an exploded front view, and (b) is a front view, and (c) is a view viewed from diagonally rearward FIG. 6 Views of rotation part of the adjuster of FIG. 4, wherein (a) is a perspective view, and (b) is a left side view, and (c) is a plan view, and (d) is a front view, and (e) is a cross-sectional view taken along a line VIe-VIe of FIG. 5(b)

As shown in FIGS. 4 and 5, the adjuster 4 includes a sliding part 8 and a rotation part 9 connected to the upper end of the sliding part 8 by an engaging protrusion 82. The stopper 4a is formed at the lower end of the sliding part 8. The sliding part 8 is slidingly movable within the long hole 3a in an up-down direction D1, but is unrotatable with respect to the intramedullary nail 3 in a circumferential direction D2. Such a configuration is realized by, for example, the long hole 3a with a substantially D-shaped cross section and the corresponding sliding part 8 with a substantially D-shaped cross section.

The rotation part 9 is a male screw member with a threaded outer peripheral surface and threadedly engages with a female screw part 3f formed on an inner surface of the long hole 3a of the intramedullary nail 3 as shown in FIG. 2. Also, the rotation part 9 is rotatable relative to the sliding part 8. When the rotation part 9 rotates relative to the intramedullary nail 3 in the circumferential direction D2, then the entire adjuster 4 moves in the up-down direction D1. At this time, the rotation part 9 moves up and down rotating, but the sliding part 8 moves up and down without rotating relative to the intramedullary nail 3. Also, a disassembly prevention ring 10 is fixed to the upper part of the female screw part 3f of the intramedullary nail 3, preventing the adjuster 4 from moving upward beyond the disassembly prevention ring 10 and becoming disengaged from the intramedullary nail 3.

Figure 6:
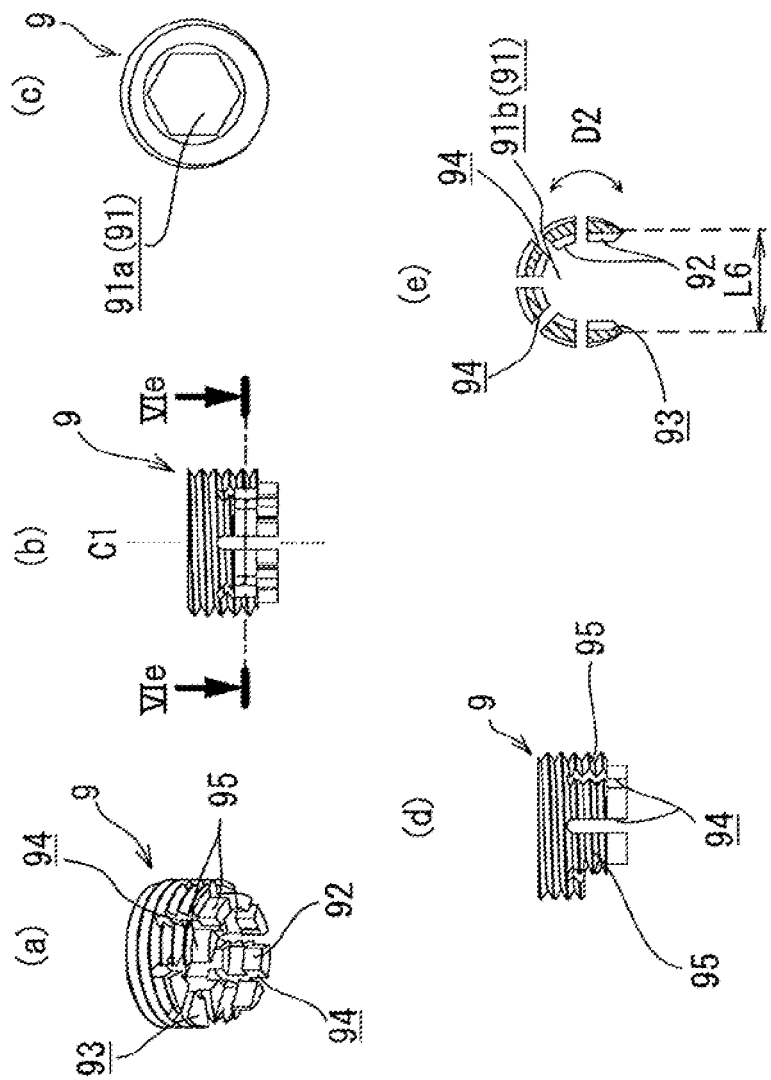

As shown in FIGS. 4 and 6, the rotation part 9 is formed with a through hole 91. An upper part of the through hole 91 functions as an operation hole 91a for insertion of an external operation tool (not shown), and a lower part of the through hole 91 functions as a receiving hole 91b for receiving an engaging part 82a to be described later. A hex wrench is used as the operation tool in this embodiment, and the operation hole 91a is formed to have a cross section in a hexagonal shape corresponding to a cross section of the hex wrench. Thus, an operator can rotate the rotation part 9 by inserting the hex wrench (not shown) into the operation hole 91*a* and rotating the same. Note that an opening of the disassembly prevention ring 10 has a larger inner diameter than the operation hole 91*a*, making the operation tool accessible to the operation hole 91*a* through the opening of the disassembly prevention ring 10.

Next, a configuration for rotatably connecting the rotation part 9 to the sliding part 8 will be described in detail. As shown in FIG. 5, the sliding part 8 has an outer shape corresponding to the long hole 3*a* of the intramedullary nail 3, and the engaging protrusion 82 is formed at the upper end of the sliding part 8. The engaging protrusion 82 has a disc-shaped engaging part 82*a* and a connecting part 82*b* with a diameter smaller than the engaging part 82*a*. The engaging part 82*a* is connected to an upper surface 81*a* of the sliding part 8 via the connecting part 82*b*. Note that a lower surface 81*b* of the sliding part 8 is a sloping surface along the through hole 3*b* (FIG. 3), and the sliding part 8 is formed with a through hole extending in a longitudinal direction (the up-down direction D1).

With reference to FIGS. 5 and 6, the receiving hole 91*b* of the rotation part 9 is a space capable of receiving the engaging part 82*a*. An inward flange part 92 is formed to an opening edge (lower edge) of the receiving hole 91*b* so as to protrude inward in the radial direction of the rotation part 9 (the adjuster 4), and a peripheral surface of the receiving hole 91*b* is formed with a cutout 93 sized for receiving the engaging part 82*a* of the engaging protrusion 82. That is, the receiving hole 91*b* of the rotation part 9 is connected outside through the cutout 93 in the radial direction, and a width dimension L6 of the cutout 93 is set larger than an outer diameter L7 of the engaging part 82*a*. Thus, the engaging part 82*a* can be received into the receiving hole 91*b* through the cutout 93 in the radial direction of the rotation part 9.

In this configuration, when the engaging part 82*a* of the engaging protrusion 82 is received into the receiving hole 91*b* through the cutout 93 of the rotation part 9 in the radial direction of the rotation part 9 (that is, in a direction of an arrow A shown in FIG. 5(*a*)) as shown in FIG. 5, then the lower surface of the engaging part 82*a* is supported by the inward flange part 92 from below. In this manner, the sliding part 8 is prevented from dropping from the rotation part 9 in the up-down direction D1, and the relative rotation between the sliding part 8 and the rotation part 9 is made possible.

With the configuration disclosed in the above-mentioned Patent Document 3, the opening should be smaller than the diameter of the ball so that the ball may not become disengaged from the space. Thus, the opening needs to deform when the ball is snapped into the space via the opening. In the present embodiment, however, the engaging part 82*a* of the sliding part 8 is easily accommodated into the receiving hole 91*b* of the rotation part 9 because the width dimension L6 of the cutout 93 is set larger than the outer diameter L7 of the engaging part 82*a*. Further, because the sliding part 8 has the substantially-D-shaped cross-section corresponding to the shape of the long hole 3*a*, the positional relationship between the engaging part 82*a* of the sliding part 8 and the receiving hole 91*b* of the rotation part 9 is made constant. Thus, the engaging part 82*a* does not become disengaged from the receiving hole 91*b*.

Here, in the configuration of the above-mentioned Patent Document 2, there is a danger that the body part is disengaged from the head part if the engagement between the head part and the body part is weak. It is considerable to slightly widen the slit as described above so that the resistance between the head part and the screw groove of the intramedullary nail is enhanced and that the fitting piece scratches more the fitting groove, thereby preventing disengagement between the body part and the head part. If the slit is widen excessively, however, then the friction between the head part and the body part becomes too large. This makes it difficult to rotate the head part relative to the body part, significantly affecting operability. On the other hand, in the present embodiment, the engaging part 82*a* of the engaging protrusion 82 is inserted into the rotation part 9 via the cutout 93 from the radial direction differing from the length direction of the sliding part 8 by 90 degrees and is supported by the inward flange part 92 from below. Thus, there is no danger that the rotation part 9 is disengaged from the sliding part 8, and stable rotation is maintained constantly.

Also, the lower portion of the rotation part 9 (the peripheral surface of the receiving hole 91*b*) is formed with a plurality of slits 94 at intervals in the circumferential direction D2, each extending in the direction of the rotation shaft C1 and penetrating the peripheral surface of the receiving hole 91*b* from the inner side to the outer side. As a result, the lower part of the rotation part 9 is formed with a plurality of fringe parts 95 at intervals in the circumferential direction. A deforming process has been performed on the plurality of fringe parts 95 (that is, the lower part of the rotation part 9) so as to deform the same by pushing and widening the same from the inside toward the outside in the radial direction.

Because the receiving hole 91*b* is formed in the fringe parts 95 at the lower part of the rotation part 9, the thickness of the fringe part 95 in the radial direction is thin. Also, the plurality of slits 94 is formed. Thus, the above-mentioned deforming process can be performed on it easier than on the head part (rotation part) of Patent Document 2. That is, the head part of Patent Document 2 is formed with only one slit penetrating the head part, requiring a relatively large force to perform the deforming process. On the other hand, according to the present embodiment, because the plurality of thin fringe parts 95 divided from each other is formed, the deforming process is possible with a smaller force, and also fine adjustment can be easily performed, making manufacturing process easy.

Also, the sliding part 8 is formed with one or a plurality of interference prevention parts 85 corresponding to the auxiliary holes 3*c* to 3*e*. The interference prevention parts 85 are interference prevention holes and/or interference prevention grooves. In this embodiment, as shown in FIG. 3, three interference prevention parts 85*a*, 85*b*, 85*c* are formed corresponding to the auxiliary holes 3*c* to 3*e*. When inserted through the intramedullary nail 3, the rotation prevention pins 61 to 63 pass the interference prevention parts 85, so interference with the sliding part 8 (the adjuster 4) is prevented.

Here, dimensions of various parts will be described with reference to FIG. 3. In this embodiment, taking effectiveness of insertion angles of the rotation prevention pins 61 to 63 relative to various types of femur fractures and manufacturability into account, a length L1 from the upper end of the intramedullary nail 3 to a center point P1 of the through hole 3*b* in the length direction and the radial direction is 40 mm or more, and a length L2 of the sliding part 8 is 21 mm or more. The invention, however, is not limited thereto.

More specifically, the lengths of the intramedullary nails 3 are non-uniform, but the intramedullary nails 3 with different lengths are used according to body constitutions of patients or the like. Although, the length L1 of a specific part, that is, between the upper end of the intramedullary nail 3 to the center point P1 of the through hole 3*b* in the length direction and the radial direction, differs according to the length of the intramedullary nail 3, the length L1 of the specific part is preferably 40 mm or more, and the length L1 of the specific part is set to 40 mm or more in this embodiment. Also, the length L2 of the sliding part 8 is a distance from the upper surface 81a of the sliding part 8 to a point of imaginary intersection P2 between the center line of the sliding part 8 extending in the length direction and the lower surface 81b. Setting the length L2 of the sliding part 8 to 21 mm or more enables insertion of the three rotation prevention pins 61 to 63 at angles effective to various types of femur fractures as described later. In this embodiment, an angle (α) between the insertion direction (orientation (second direction)) of the rotation prevention pins 62, 63 and the insertion direction (orientation (first direction)) of the lag screw 2 is 10 degrees to 20 degrees.

That is, in order to insert the rotation prevention pins 61 to 63 with required thickness, a distance L3 from the lower surface 81b of the sliding part 8 (the point of imaginary intersection P2) to the interference prevention part 85a is preferably 7 mm, and a distance L4 from the interference prevention part 85a to the interference prevention part 85b is preferably 7 mm, and a distance L5 from the interference prevention part 85b to the interference prevention part 85c is preferably 3.5 mm. Also, because the sliding part 8 is a member that slid-moves in the up-down direction, it is preferable that each interference prevention part 85 have a length of 3.5 mm or more in the up-down direction, taking the sliding amount of the sliding part 8 into consideration. Thus, it is preferable that the length L2 be 21 mm or more. In this embodiment, the length L2 of the sliding part 8 is set to 21 mm or more, enabling insertion of the three rotation prevention pins 61 to 63 effective to various femur fractures.

Also, the end cap 5 is formed with a protrusion 52 protruding downward from the male screw part 51. The protrusion 52 has a smaller diameter than the male screw part 51. When the end cap 5 is fitted to the intramedullary nail 3, the protrusion 52 is inserted into the operation hole 91a of the rotation part 9 via the disassembly prevention ring 10. Because the protrusion 52 functions as a guide when the end cap 5 is fitted to the intramedullary nail 3, the end cap 5 is more easily fitted to the intramedullary nail 3 compared to those without the protrusion 52.

The femur fixation apparatus 1 with the above-described configuration is fitted to femur in a manner described next. With reference to FIGS. 2 and 7, the intramedullary nail 3 with the adjuster 4 prefixed thereto is inserted into marrow of the femoral shaft T1 to a predetermined depth from the above in the drawings. Next, the lag screw 2 is inserted through the through hole 3b of the intramedullary nail 3 into the femur T to a necessary depth toward the femoral head T2. In this state, the rotation part 9 of the adjuster 4 is rotated in a predetermined direction with an operation tool (not shown (a hex wrench, for example)), lowering the entire adjuster 4. The stopper 4a is engaged into the groove 22, preventing the rotation of the lag screw 2 in the circumferential direction D3.

Because the width dimension W of the grooves 22 gradually increases toward the one end of the lag screw 2 formed with the male screw part 21, the stopper 4a is allowed to slide-move within the groove 22 toward the one end in a direction indicated by an arrow Y but is prevented to move toward the other end in a direction indicated by an arrow Z. This means that the lag screw 2 is prevented from moving in the direction of the arrow Y relative to the intramedullary nail 3. In this manner, the lag screw 2 is prevented from accidentally moving in the direction of the arrow Y relative to the intramedullary nail 3 and projecting out from the femoral head T2.

Also, because the above-mentioned deforming process has been performed on the rotation part 9 of the adjuster 4, the fringe parts 95 catch on the female screw part 3f of the intramedullary nail 3, making the rotation part 9 hard to rotate without a certain amount of force applied thereon with the operation tool or the like. This configuration prevents the rotation part 9 from accidentally rotating and from lifting up the adjuster 4 to disengage the stopper 4a from the groove 22.

Next, the rotation prevention pins 61 to 63 are inserted through the auxiliary holes 3c to 3e (FIG. 1) into the femur T. At this time, the rotation prevention pins 61 to 63 are smoothly inserted without interfered with the adjuster 4 because the interference prevention parts 85 are formed in the adjuster 4. Here, because the sliding part 8 with the interference prevention parts 85 moves up and down without rotating, change of the orientation of the interference prevention parts 85 due to rotation of the sliding part 8 is prevented.

It should be noted that the operator does not necessarily use all of the rotation prevention pins 61 to 63, but may use any one or more of them depending on the fracture type and condition or use none of them.

The rotation prevention pin 61 inserted in the above-described manner extends substantially parallel to the lag screw 2 at a position higher than the lag screw 2. Also, the rotation prevention pins 62, 63 are located higher than the rotation prevention pin 61 and extend diagonally relative to the lag screw 2 (and the rotation prevention pin 61) in the front view in FIG. 7. In the embodiment, because the length L2 of the sliding part 8 is 21 mm or more as described above, the angle (α) of the insertion direction (orientation (the second direction)) of the rotation prevention pins 62, 63 relative to the insertion direction (orientation (the first direction)) may be set to any angle between 0 degree to 20 degrees. The angle (α), however, is preferably 10 degrees to 20 degrees. Setting the angle (α) to 10 degrees or more enables insertion of the rotation prevention pins 61 to 63 at insertion angles effective to various types of femur fractures, with combinations of the rotation prevention pins 61 to 63. This enables to fix fractures from greatly various angles compared to the conventional one.

Also, the rotation prevention pins 62, 63 extend diagonally relative to each other such that their tip end sections intersect sideways in the plan view.

As described above, in the embodiment, the rotation prevention pins 62, 63 extending diagonally in the length direction relative to the lag screw 2 can be used in addition to the rotation prevention pin 61. Thus, the rotation prevention pins 62, 63 can be inserted at an angle perpendicular or nearly perpendicular to a diagonally-extending fracture line, fixing the fractures more effectively.

Figure 17:
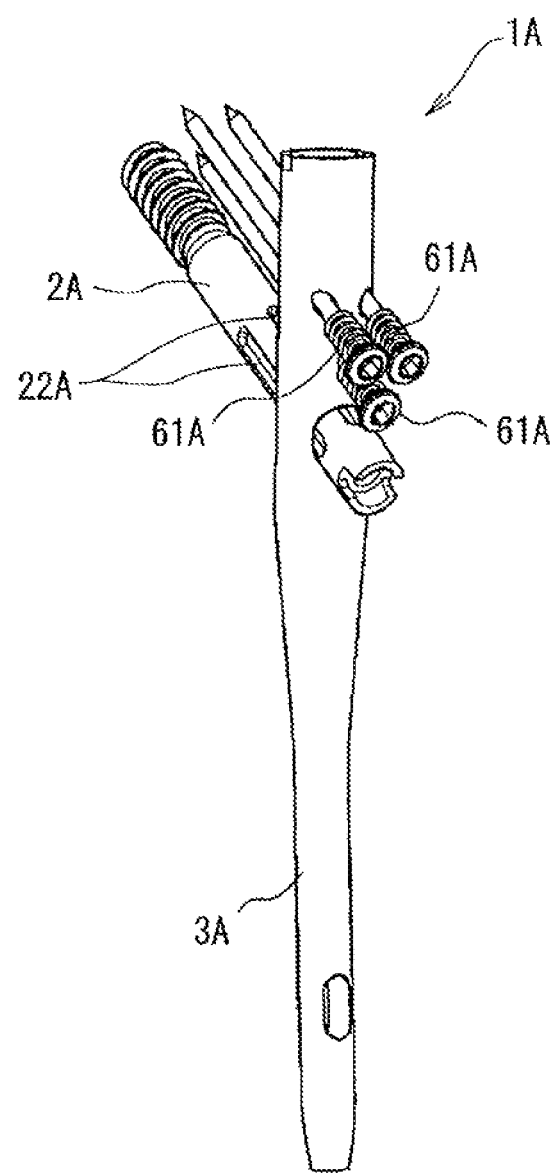
Figure 18:
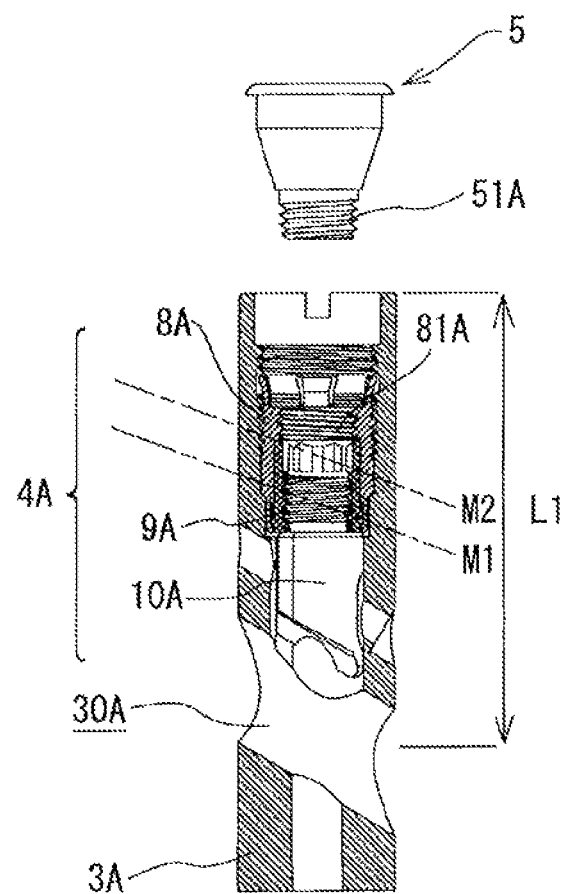

Here, in the conventional femur fixation apparatus 1A shown in FIGS. 17 and 18, it is difficult to set the angle of the rotation-prevention pin 61A relative to the lag screw 2A in the length direction large for the following reasons.

With reference to FIG. 18, the adjuster 4A of the conventional femur fixation apparatus 1A is configured to include the cylindrical part 8A, the rotation part 9A, and the sliding part 10A as described above. The sliding part 10A is formed with the interference prevention hole for preventing interference with the rotation-prevention pin 61A. In this configuration, in order to insert a pair of rotation-prevention pins 61A, 61A into the intramedullary nail 3A at the same positions and angles as the rotation prevention pins 62, 63 of the embodiment, the rotation-prevention pins 61A, 61A need to pass through the cylindrical part 8A and the rotation part 9A of the adjuster 4A as indicated by imaginary lines M1, M2 in FIG. 18. However, forming the interference prevention hole in the rotation part 9A that is operated to rotate cannot reliably prevent the interference with the rotation prevention pins 61A, 61A.

It is conceivable to set the length of the sliding part 10A larger to enlarge, in the longitudinal direction (vertical direction), an area where the rotation-prevention pin 61A can pass through. However, enlarging the length of the sliding part 10A enlarges the length of the entire adjuster 4A. On the other hand, the length L1 cannot be increased according to the adjuster 4A because the length L1 between the upper end of the intramedullary nail 3A and the center point of the insertion hole 30A of the lag screw 2A should be determined based on the body constitution of patients. If the length L1 is increased regardless of the body constitution of patients, there is a danger that the upper part of the intramedullary nail 3A inserted into the femur protrudes from the femur. Thus, in the adjuster 4A having the sliding part 10A with the limited length, the angle of the rotation-prevention pin 61A relative to the lag screw 2A in the vertical direction needs to be shallow.

On the other hand, in the adjuster 4 of the embodiment, the rotation part 9 is threadedly engaged directly with the intramedullary nail 3 without the cylindrical part 8A. Thus, the length of the sliding part 8 (part where the interference prevention part 85 for preventing interference with the rotation prevention pins 61 to 63 is formed) can be longer than the conventional ones, without increasing the length of the adjuster 4. As a result, an area where the interference prevention part 85 can be formed (an area where the rotation prevention pins 61 to 63 can penetrate through) can be large. Thus, the rotation prevention pins 62, 63 can be inserted at a large angle with respect to the lag screw 2 in the vertical direction.

Also, in the conventional femur fixation apparatus 1A shown in FIG. 18, the male screw part 51A of the end cap 5A is configured to threadedly engage with the female screw part 81A formed in the cylindrical part 8A. In the embodiment, on the other hand, the female screw part 31 that the end cap 5 threadedly engages with is formed in the inner surface of the intramedullary nail 3 as shown in FIG. 3. With this configuration, the length of the end cap 5 can be shorter in the vertical direction compared to the conventional end cap 5A shown in FIG. 18. Thus, the position of the rotation part 9 in the intramedullary nail 3 can be higher by that amount. With this configuration also, the length of the sliding part 8 of the adjuster 4 in the vertical direction (that is, the area where the rotation prevention pins 61 to 63 can penetrate through) can be increased.

As described above, in the femur fixation apparatus 1 according to the embodiment, the length L2 of the sliding part 8 is set long (21 mm or more, for example), so the insert direction of the rotation prevention pins 62, 63 can be greatly angled from the lag screw 2 in the vertical direction. This widens the choice of fixing methods (fixing directions) according to the fracture types. Also, because the adjuster 4 includes less number of components, the production costs of the adjuster 4 and thus the entire femur fixation apparatus 1 can be suppressed. Also, the less number of components makes it easier to achieve uniform quality.

Second Embodiment

Next, a femur fixation apparatus according to a second embodiment of the invention will be described. The femur fixation apparatus according to this embodiment is substantially the same as the femur fixation apparatus 1 described above, but differs in including an adjuster 104 shown in FIG. 8 instead of the adjuster 4. Thus, only the adjuster 104 will be described here, and the description of the remaining will be omitted. Also, in this embodiment and following embodiments, parts and components that are substantially the same as those of the first embodiment are designated by the same reference numerals and description thereof will be omitted.

Figure 8:
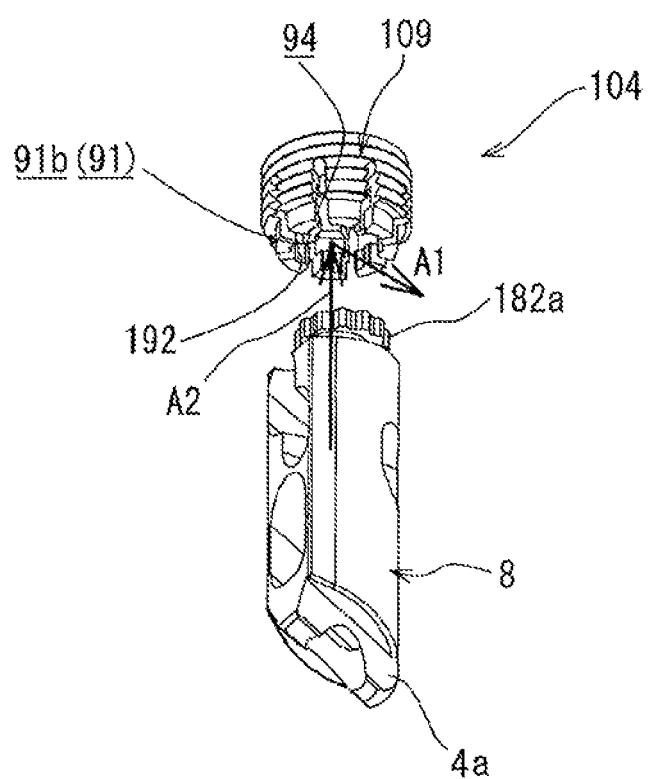
FIG. 8 An exploded perspective view of an adjuster of a femur fixation apparatus according to a second embodiment of the invention FIG. 9 Views of a sliding part of the adjuster of FIG. 8, wherein (a) is a plan view, and (b) is a front view.
Figure 9:
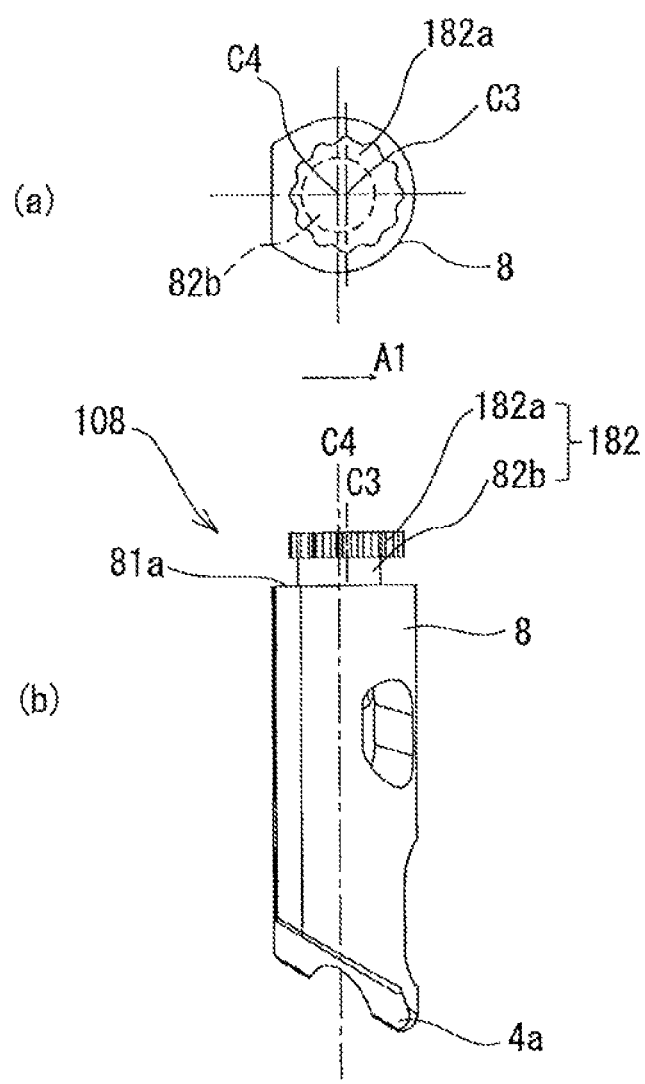

With reference to FIGS. 8 and 9, the adjuster 104 of the embodiment includes the sliding part 8 and a rotation part 109 connected to the sliding part 8 via an engaging protrusion 182. The stopper 4a is formed to the lower end of the sliding part 8.

The engaging protrusion 182 is formed to the upper end of the sliding part 8, and includes a plate-shaped engaging part 182a and the connecting part 82b with a smaller diameter than the engaging part 182a. The engaging part 182a is connected to the upper surface 81a of the sliding part 8 via the connecting part 82b. The engaging part 182a preferably has a horizontal cross-section with a contour in the shape other than the circle. In the example shown in FIG. 9(a), it has a corrugated contour. Also, the radial center C3 of the engaging part 182a (axial line extending in the up-down direction) is deviated sideways from the radial center C4 of the sliding part 8 as indicated by an arrow A1.

Figure 10:
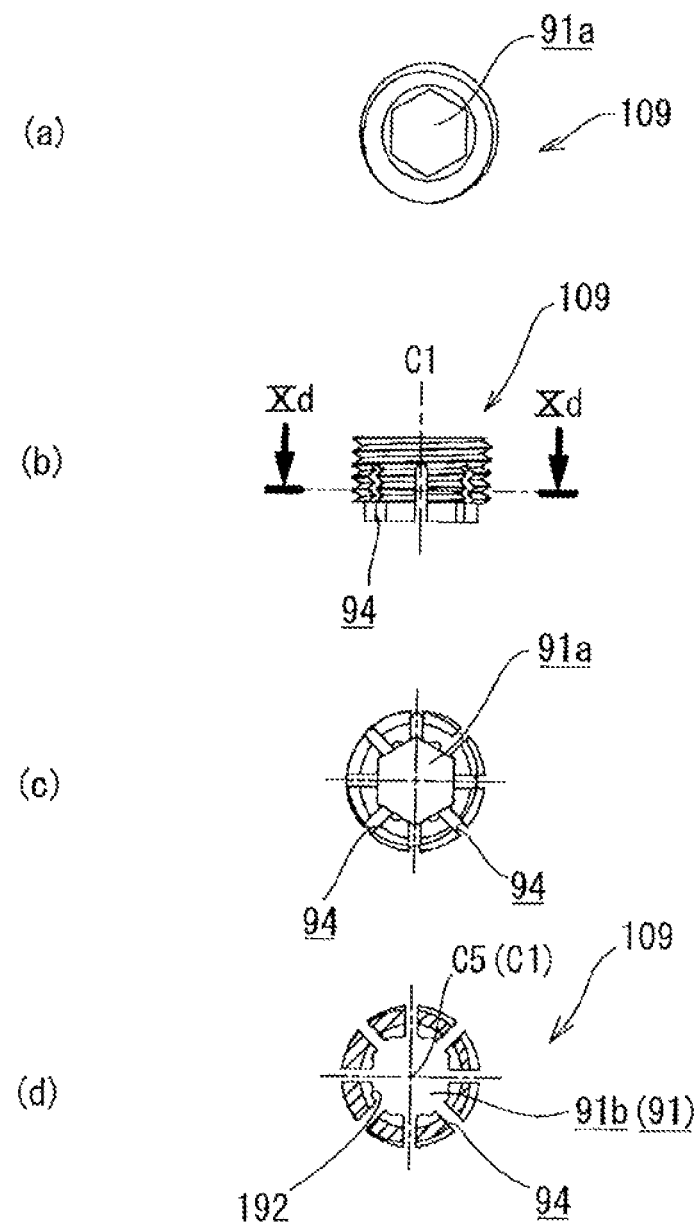
FIG. 10 Views of a rotation part of the adjuster of FIG. 8, wherein (a) is a plan view, and (b) is a front view, and (c) is a bottom view, and (d) is a cross-sectional view taken along a line Xd-Xd of FIG. 10(b)

As shown in FIG. 10, the rotation part 109 is similar to the above-described rotation part 9, but differs in that the rotation part 109 is formed with an inward flange part 192 at the opening edge (lower edge) thereof, instead of the inward flange part 92, and that no cutout is formed in the rotation part 109. The flange part 192 has an inner edge sized and shaped corresponding to the contour (corrugated contour, in this embodiment) of the engaging part 182a. The radial center C5 of the opening of the receiving hole 91b defined by the inner edge of the flange part 192 is located on the rotation axis C1 of the rotation part 109.

With this configuration, in order to connect the sliding part 8 to the rotation part 109, the engaging part 182a of the engaging protrusion 182 is inserted into the receiving hole 91b of the rotation part 109 from below in the direction of an arrow A2, and then the sliding part 8 is shifted in the direction of the arrow A1 relative to the rotation part 109. As a result, the engaging part 182a is supported by the flange part 192 from below, and the sliding part 8 is allowed to idly rotate relative to the rotation part 109. That is, because the radial center C3 of the engaging part 182a is deviated from the radial center C5 of the opening of the receiving hole 91b, even when the rotation part 109 rotates relative to the engaging protrusion 182 and the sliding part 8, the lower surface of the engaging part 182a partially and constantly contacts the upper surface of the flange part 192. Thus, the engaging part 182a does not become disengaged from the flange part 192. Also, with the engaging part 182a having the horizontal cross-section with the contour in the shape other than the perfect circle, parts of the flange part 192 that support the engaging part 182a are distributed in the circumferential direction, preventing the engaging part 182a from becoming a cantilever state.

The embodiment having this configuration can achieve the same effects as the first embodiment described above.

Third Embodiment

Next, a femur fixation apparatus according to a third embodiment of the invention will be described. The femur fixation apparatus according to this embodiment is substantially the same as the above-described femur fixation apparatus 1, but differs in including an adjuster 204 shown in FIG. 11 instead of the adjuster 4. Thus, only the adjuster 204 will be described here.

Figure 11:
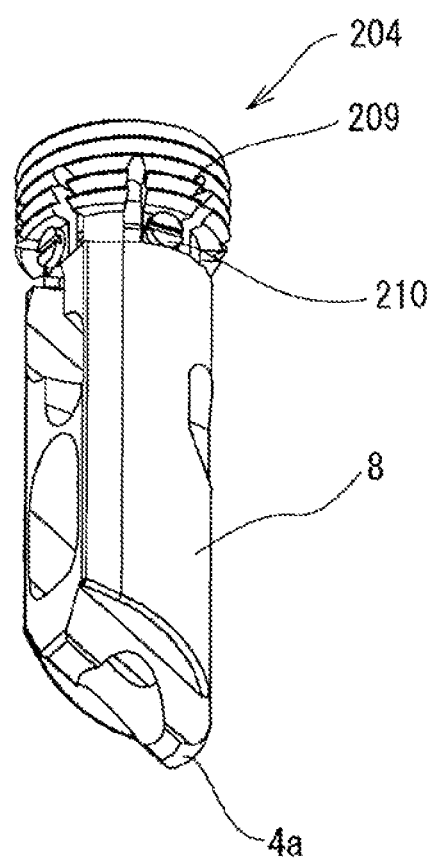
FIG. 11 A perspective view of an adjuster of a femur fixation apparatus according to a third embodiment of the invention FIG. 12 Views of a rotation part of the adjuster of FIG. 11, wherein (a) is a plan view, and (b) is a front view, and (c) is a bottom view, and (d) is a cross-sectional view taken along a line XIId-XIId of FIG. 10(b).
Figure 12:
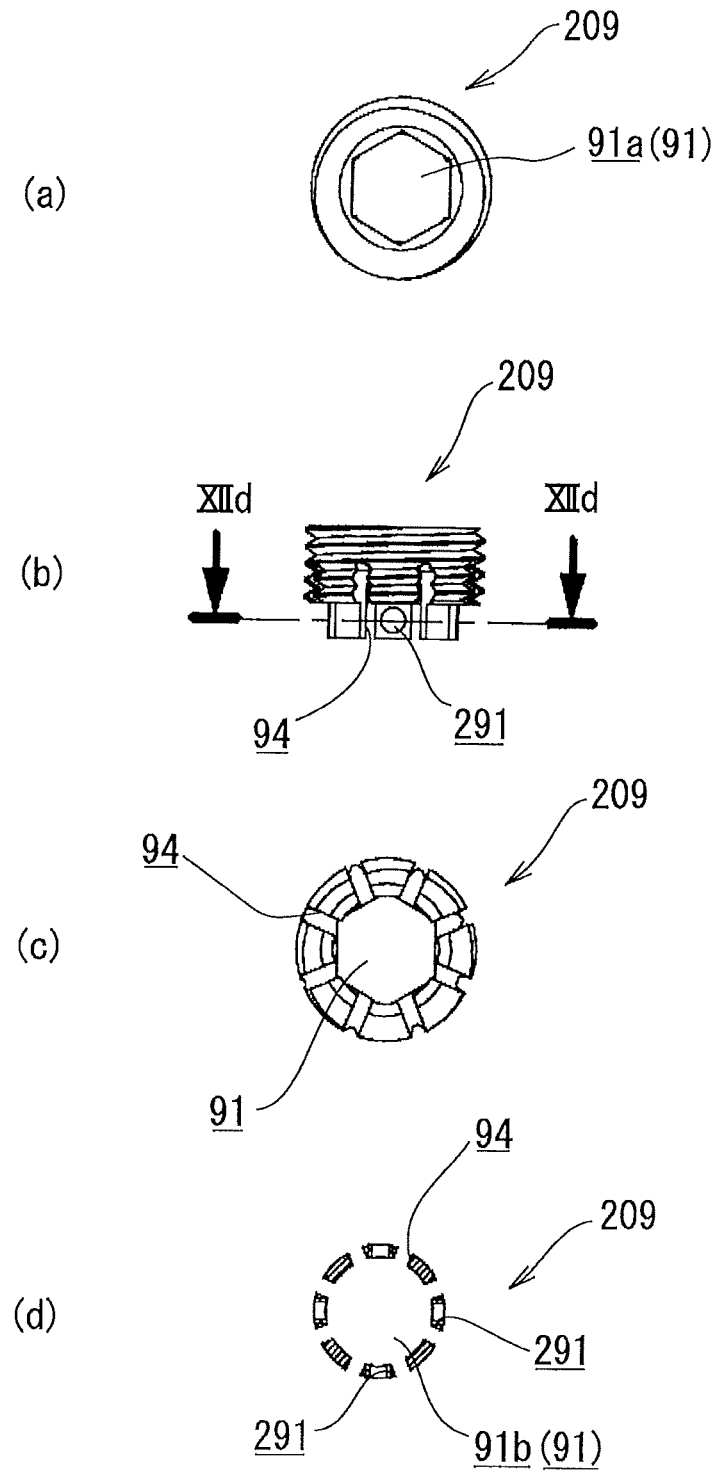

As shown in FIG. 11, the adjuster 204 includes a rotation part 209 and the sliding part 8, and the engaging protrusion 82 (see FIG. 5) is formed at the upper end of the sliding part 8 as in the first embodiment. The rotation part 209 is similar to the above-described rotation part 109, but differs in that, instead of the inward flange part 192, a plurality of screw holes 291 for insertion of set screws 210 is formed at the lower end of the rotation part 209 so as to penetrate through the peripheral surface of the receiving hole 91b as shown in FIG. 12.

The engaging part 82a of the engaging protrusion 82 is received into the receiving hole 91b of the rotation part 209 from the bottom. The set screws 210 shown in FIG. 13 are threadedly engaged with the corresponding screw holes 291. As a result, the engaging part 82a (FIG. 5) is supported by the tip ends of the set screws 210 from the bottom, preventing the sliding part 8 from becoming disengaged from the rotation part 209 while allowing the sliding part 8 to rotate relative to the rotation part 209. Thus, this embodiment achieves the same effects as described above.

[Modifications]

Next, a modification of the first embodiment will be described with reference to FIG. 14. In the above-described first embodiment, the sliding part 8 is formed with the engaging protrusion 82, and the rotation part 9 is formed with the receiving hole 91b, and the engaging part 82a of the engaging protrusion 82 is supported by the inward flange part 92 from the bottom. In this modification, however, as shown in FIG. 14, the engaging protrusion 82 is formed at the lower end of a rotation part 309, and the receiving hole 91b is formed at the upper end of a sliding part 308, and the engaging part 82a of the engaging protrusion 82 is connected to a lower surface of the rotation part 309 via the connecting part 82b. Note that the configuration of the rotation part 309 is substantially the same as that of the rotation part 9 other than being formed with the engaging protrusion 82 instead of the receiving hole 91b, and the configuration of the sliding part 308 is substantially the same as that of the sliding part 8 other than being formed with the receiving hole 91b instead of the engaging protrusion 82.

In this configuration, when the engaging part 82a of the engaging protrusion 82 is inserted into the receiving hole 91b via the cutout 93 in the radial direction, then the inward flange part 92 is supported by the engaging part 82a from the bottom, achieving the same effects as the first embodiment.

That is, it is preferable that one of the sliding part and the rotation part be formed with the engaging protrusion 82 and the other be formed with the receiving hole 91b and that the engaging part 82a of the engaging protrusion 82 be inserted into the receiving hole 91b via the cutout 93 in the radial direction of the adjuster so that the engaging part 82a confronts the inward flange part 92 in the longitudinal direction, thereby freely-rotatably connecting the sliding part with the rotation part.

Figure 15:
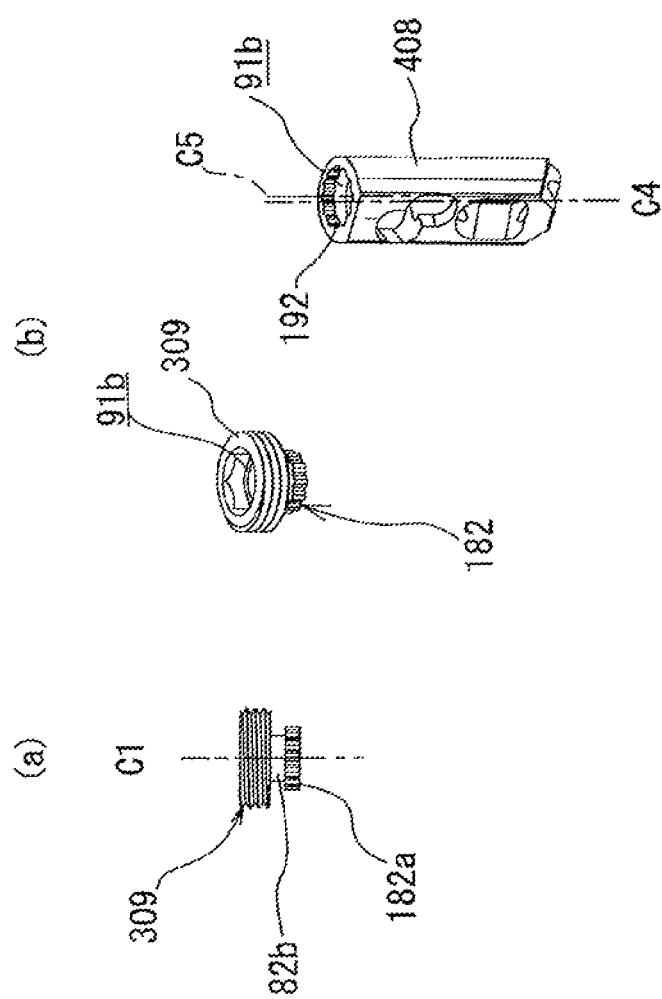

Next, a modification of the second embodiment will be described with reference to FIG. 15. In the above-described second embodiment, the sliding part 8 is formed with the engaging protrusion 182, and the rotation part 109 is formed with the receiving hole 91b, and the engaging part 182a of the engaging protrusion 182 is supported by the inward flange part 192 from the bottom. In this modification, however, as shown in FIG. 15, the engaging protrusion 182 is formed at the bottom end of the rotation part 309, and the receiving hole 91b is formed at the upper end of a sliding part 408, and the inward flange part 192 is formed to the opening edge (upper end) of the receiving hole 91b. The engaging part 182a of the engaging protrusion 182 is connected to the bottom surface of the rotation part 309 via the connecting part 82b, and the radial center of the engaging part 182a is located on the rotation axis C1 of the rotation part 309. Also, the radial center C5 of the inward flange part 192 is deviated sideway (in the radial direction) from the radial center C4 of the sliding part 408. Note that the configuration of the sliding part 408 is substantially the same as that of the sliding part 8 other than being formed with the receiving hole 91b instead of the engaging protrusion 82.

With this configuration, in order to connect the sliding part 408 to the rotation part 309, the engaging part 182a is inserted into the receiving hole 91b from above, and then the rotation part 309 is shifted in the radial direction with respect to the sliding part 408. As a result, the inward flange part 192 is supported by the engaging part 182a from the bottom.

That is, it is preferable that one of the sliding part and the rotation part be formed with the engaging protrusion 182 and the other be formed with the receiving hole 91b, and that the inward flange part 192 be formed such that the radial center of the opening of the receiving hole 91b defined by the inner edge of the inward flange part 192 is deviated from the radial center of the engaging part 182a of the engaging protrusion 182. With this configuration, by inserting the engaging part 182a of the engaging protrusion 182 into the receiving hole 91b in the longitudinal direction of the adjuster and then shifting the same in the radial direction, the engaging part 182a is brought into confrontation with the inward flange part 192 in the longitudinal direction. As a result, the sliding part is freely-rotatably connected to the rotation part.

Thus, in another modification of the second embodiment, the inward flange part 192 is formed at the opening edge of the receiving hole 91b of the rotation part 109, and the radial center of the opening of the receiving hole 91b is deviated from the radial center C1 of the rotation part 109, and the radial center C5 of the engaging part 182a of the engaging protrusion 182 formed at the upper end of the sliding part 8 matches the radial center C4 of the sliding part 8.

Further, in a still another modification of the second embodiment, the engaging protrusion 182 is formed at the lower end of the rotation part 309, and the radial center of the engaging part 182a of the engaging protrusion 182 is deviated from the radial center C1 of the rotation part 309, and the inward flange part 192 is formed at the opening edge of the receiving hole 91b formed in the upper end of the sliding part 408, and the radial center of the opening of the receiving hole 91b matches the radial center C4 of the sliding part 408.

Figure 16:
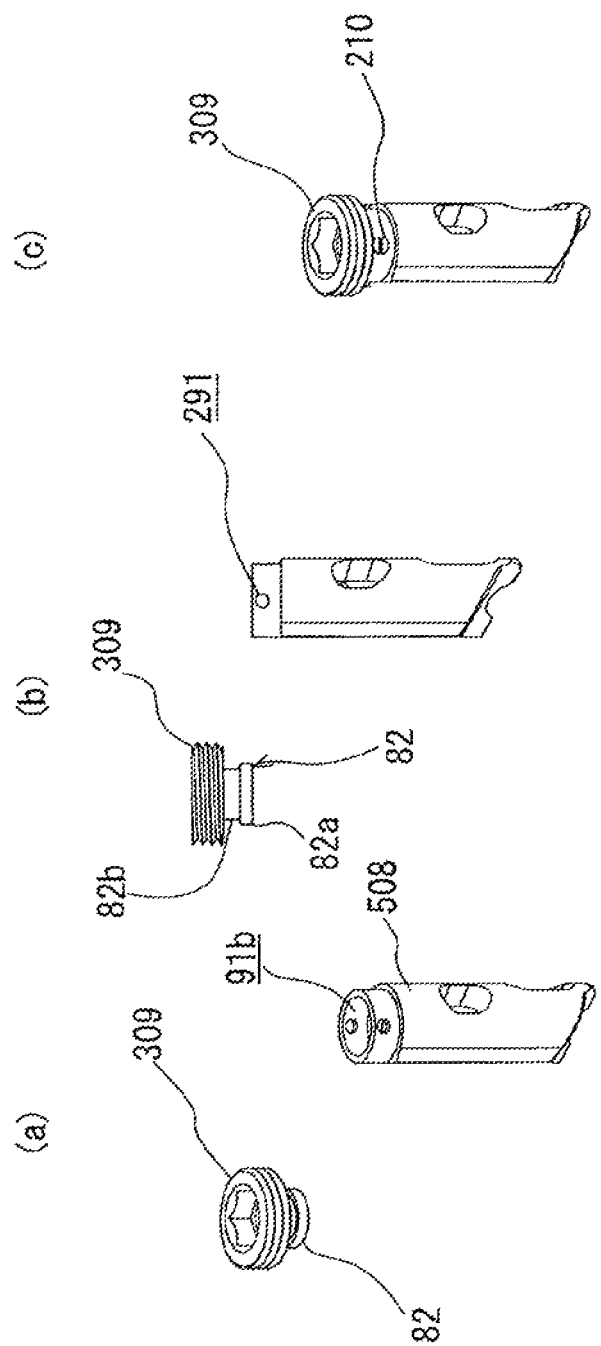

Next, a modification of the third embodiment will be described with reference to FIG. 16. In the above-described third embodiment, the engaging protrusion 82 is formed to the sliding part 8, and the receiving hole 91b is formed in the rotation part 209, and the engaging part 82a received in the receiving hole 91b is supported by tip ends of the set screws 210 inserted through the peripheral surface of the receiving hole 91b from the bottom. In this modification, however, as shown in FIG. 16, the engaging protrusion 82 is formed to the lower end of the rotation part 309, and the receiving hole 91b is formed in the upper end of a sliding part 508, and tip ends of the set screws 210 inserted through the peripheral surface of the receiving hole 91b are supported by the engaging part 82a of the engaging protrusion 82 from the bottom. This configuration also achieves the same effects as the third embodiment described above.

That is, it is preferable that one of the sliding part and the rotation part be formed with the engaging protrusion 82, and the other be formed with the receiving hole 91b, and the sliding part be freely-rotatably supported by the rotation part via the engaging protrusion 82 with the tip ends of the plurality of set screws 210 inserted through the opening edge of the receiving hole 91b confronting, in the longitudinal direction of the adjuster, the engaging part 82a of the engaging protrusion 82 received in the receiving hole 91b.

While the femur fixation apparatuses according to the embodiments of the invention and modifications thereof have been described with reference to the drawings, the invention is not limited to these embodiments and modifications, but various changes and modifications may be made therein without departing from the spirit of the invention.

For example, in the above-described embodiments, the width dimension W of the grooves 22 of the lag screw 2 becomes wider toward the one end and narrower toward inside in the radial direction of the lag screw 2, thereby preventing slide-movement of the stopper 4a in the direction of the arrow Z (FIG. 2). In another aspect of the invention, however, the slide-movement of the stopper 4a in the direction of the arrow Z is prevented by setting the width dimension W of the grooves 22 uniform along the entire length of the grooves 22 and deepening the grooves 22 toward the one end of the lag screw 2.

Also, in the above-described embodiments, the rotation prevention pins 61 to 63 are used as a rotation prevention member. According to another aspect of the invention, a rotation prevention screw is preferably used as the rotation prevention member.

In the above-described first to third embodiments, upper part of the through hole 91 formed in the rotation part 9 (109, 209) functions as the operation hole 91a, and the lower part thereof functions as the receiving hole 91b, and the operation hole 91a is in fluid communication with the receiving hole 91b. However, the operation hole 91a is not necessarily in fluid communication with the receiving hole 91b.

In the example shown in FIG. 6, the lower part of the outer peripheral surface of the rotation part 9 functions as an unthreaded small-diameter part. In a different embodiment, however, it is preferable that the rotation part 9 have a uniform outer diameter and an entire outer peripheral surface thereof is threaded.

EXPLANATION OF REFERENCE NUMBERS 1 femur fixation apparatus
2 lag screw
3 intramedullary nail
4, 104, 204 adjuster
5 end cap (cover member)
8, 108 sliding part
9, 109, 209 rotation part
61, 62, 63 rotation prevention pin (rotation prevention member)
82 engaging protrusion
82a engaging part
82b connecting part

The invention claimed is:
1. A femur fixation apparatus comprising:
an intramedullary nail formed with at least one auxiliary hole for insertion of a rotation prevention member;
a lag screw that is inserted through the intramedullary nail; and
an adjuster fitted in the intramedullary nail, wherein:
the adjuster includes a sliding part unrotatable and slide-movable in a longitudinal direction relative to the intramedullary nail and a rotation part rotatably connected to an upper part of the sliding part, the sliding part being formed with an interference prevention part for preventing interference with the rotation prevention member inserted through the auxiliary hole, the sliding part being formed at a lower end with a stopper that prevents rotation of the lag screw, the rotation part rotatably and threadedly engaged inside the intramedullary nail;
the sliding part is formed with an engaging protrusion;
the rotation part is formed with a receiving hole;
the engaging protrusion includes an engaging part and a connecting part with a smaller diameter than the engaging part, the connecting part connecting the engaging part with the rotation part;
an opening edge of the receiving hole is formed with an inward flange part, and a peripheral surface of the receiving hole is formed with a cutout and a plurality of slits, the cutout being for receiving the engaging part from a radial direction of the adjuster, the plurality of slits being extending in the longitudinal direction and penetrating the peripheral surface from the inside to the outside;
when the engaging part is inserted in the receiving hole via the cutout from the radial direction of the adjuster, the inward flange part supports the engaging part from the bottom, and the sliding part is rotatably connected to the rotation part; and
a deforming process has been performed on the rotation part for deforming the lower part thereof formed with the plurality of slits to widen the same from inside to outside in the radial direction.

2. A femur fixation apparatus comprising:
an intramedullary nail formed with at least one auxiliary hole for insertion of a rotation prevention member;
a lag screw that is inserted through the intramedullary nail; and
an adjuster fitted in the intramedullary nail, wherein:
the adjuster includes a sliding part unrotatable and slide-movable in a longitudinal direction relative to the intramedullary nail and a rotation part rotatably connected to an upper part of the sliding part, the sliding part being formed with an interference prevention part for preventing interference with the rotation prevention member inserted through the auxiliary hole, the sliding part being formed at a lower end with a stopper that prevents rotation of the lag screw, the rotation part rotatably and threadedly engaged inside the intramedullary nail;
one of the sliding part and the rotation part is formed with an engaging protrusion;
the other of the sliding part and the rotation part is formed with a receiving hole;
the engaging protrusion includes an engaging part and a connecting part with a smaller diameter than the engaging part, the connecting part connecting the engaging part with the one of the sliding part and the rotation part;
an opening edge of the receiving hole is formed with an inward flange part, and a radial center of the engaging part is deviated from a radial center of an opening of the receiving hole; and
the engaging part is inserted into the receiving hole in the longitudinal direction and then shifted in a radial direction of the adjuster to confront the inward flange part in the longitudinal direction, thereby rotatably connecting the slide part with the rotation part.

3. A femur fixation apparatus comprising:

an intramedullary nail formed with at least one auxiliary hole for insertion of a rotation prevention member;

a lag screw that is inserted through the intramedullary nail; and an adjuster fitted in the intramedullary nail, wherein:

the adjuster includes a sliding part unrotatable and slide-movable in a longitudinal direction relative to the intramedullary nail and a rotation part rotatably connected to an upper part of the sliding part, the sliding part being formed with an interference prevention part for preventing interference with the rotation prevention member inserted through the auxiliary hole, the sliding part being formed at a lower end with a stopper that prevents rotation of the lag screw, the rotation part rotatably and threadedly engaged inside the intramedullary nail;

one of the sliding part and the rotation part is formed with an engaging protrusion;

the other of the sliding part and the rotation part is formed with a receiving hole;

the engaging protrusion includes an engaging part and a connecting part with a smaller diameter than the engaging part, the connecting part connecting the engaging part with the one of the sliding part and the rotation part;

a plurality of set screws is radially-inwardly inserted through an opening edge of the receiving hole; and the sliding part is rotatably supported by the rotation part with the engaging part received in the receiving hole confronting tip ends of the plurality of set screws in the longitudinal direction.

* * * * *